United States Patent [19]

Money

[11] Patent Number: 5,782,744
[45] Date of Patent: Jul. 21, 1998

[54] IMPLANTABLE MICROPHONE FOR COCHLEAR IMPLANTS AND THE LIKE

[76] Inventor: David Money, 50 Blackbutt Avenue, Pennant Hills, NSW 2120, Australia

[21] Appl. No.: 567,261

[22] Filed: Dec. 5, 1995

[30] Foreign Application Priority Data

Nov. 13, 1995 [AU] Australia ............... PCT/AU95/00753

[51] Int. Cl.$^6$ ........................................... H04R 25/00
[52] U.S. Cl. ................................... 600/25; 607/57
[58] Field of Search ..................... 600/25; 607/55–57; 381/68

[56] References Cited

U.S. PATENT DOCUMENTS

| | | | |
|---|---|---|---|
| 4,207,441 | 6/1980 | Ricard et al. | 179/107 |
| 4,850,962 | 7/1989 | Schaefer | 600/25 |
| 5,061,282 | 10/1991 | Jacobs et al. | 600/25 |
| 5,085,628 | 2/1992 | Engebretson et al. | 600/25 |
| 5,176,620 | 1/1993 | Gilman | 600/25 |
| 5,344,387 | 9/1994 | Lupin | 600/25 |
| 5,411,467 | 5/1995 | Hortmann et al. | 600/25 |
| 5,531,787 | 7/1996 | Lesinski et al. | 600/25 |
| 5,569,307 | 10/1996 | Schulman et al. | 607/57 |
| 5,571,148 | 11/1996 | Loeb et al. | 607/57 |

FOREIGN PATENT DOCUMENTS

| | | |
|---|---|---|
| 4221866A1 | 5/1994 | Germany. |
| WO9105523 | 5/1991 | WIPO. |

*Primary Examiner*—Jennifer Bahr
*Assistant Examiner*—Bryan K. Yarnell
*Attorney, Agent, or Firm*—Gottlieb, Rackman & Reisman

[57] ABSTRACT

A system and method for assisting a person with a hearing disability includes an implantable microphone which senses sounds by monitoring pressure variations in the cochlear fluid. The electrical signal generated by the microphone is processed and used by a signal generator, such as cochlear implant to generate excitation signals for the patient. In this manner, external microphones, used in prior art systems, are eliminated.

21 Claims, 4 Drawing Sheets

IMPLANTABLE MICROPHONE FOR COCHLEAR IMPLANTS AND THE LIKE

BACKGROUND OF THE INVENTION

A. Field of Invention

This invention pertains to a microphone which may be implanted in the ear of a patient. The microphone is preferably used in conjunction with a cochlear implant, although it may be used for other purposes as well.

B. Description of the Prior Art

The subject invention pertains primarily to cochlear implant systems. These cochlear systems are used to provide therapy to a patient suffering from hearing loss. All of these systems require two sections: an internal or implanted section, and an external section. The external section includes a microphone for receiving ambient sounds and converting them to electrical signals. These electrical signals are processed and sent to the implanted section. The implanted section then generates excitation signals used to electrically excite the cochlear nerve of the patient through an electrode array.

A major disadvantage of these systems is that the external section is fairly visible and thus provides a source of embarrassment to the patient. Additionally, a communication channel must be established between the external and internal section either by a hard-wired connection or by using electromagnetic means such as radio waves or inductive coupling. In either case additional circuitry is required increasing the complexity of the system. Moreover, the direct coupling requires a mechanical connection through the patient's skin which may lead to infections and other complications. These problems could be eliminated by providing a fully implanted cochlear system, i.e., a system wherein the microphone is not external but is surgically implanted. Some early attempts have been made in this direction, for example by implanting a microphone which uses the ear drum as the microphone membrane with either electromagnetic or piezoelectric sensing of the membrane motion in response to ambient sound. However, none of the solutions proposed proved to be satisfactory because they require very high degree of precision in making the mechanical components.

U.S. Pat. No. 4,850,962 to Schaeffer proposes a mechanical to electrical transducer coupled to the tympanic membrane or some other part of the ossicular chain.

U.S. Pat. No. 4,988,962 to Engebretson shows a system conveying sound vibrations from the malleus to a transducer.

U.S. Pat. No. 5,176,620 to Gilman describes a hearing aid which transmits electrical signals from an external microphone and transmits it to the cochlear fluid.

OBJECTIVES AND SUMMARY OF THE INVENTION

In view of the above-mentioned disadvantages of the prior art, it is an objective of the present invention to provide an implantable microphone which can be used in conjunction with an excitation means such as a cochlear implant to enable a patient to perceive sounds.

A further objective is to provide a completely implantable cochlear implant whereby the external components of previous such aids are eliminated.

Yet a further objective is to provide an implantable microphone constructed and arranged to take advantage, as much as possible, of the patient's natural organs.

Other objectives and advantages of the invention shall be discussed in the following description. Briefly, the subject application takes advantage of the fact that patients suitable for cochlear implants usually have a normally functioning eardrum and ossicular chain and consequently the fluid within the patient's cochlea responds to external sounds the same way as in a normal person. The deficiency in these persons is related to the nervous system receiving signals from the fluid. Advantageously, in the present invention, the normally occurring pressure variations within the cochlear fluid are translated into electrical signals by a microphone in communication with the fluid pressure and transmitted to the cochlear implant for further processing. The pressure variations are transmitted efficiently to the microphone due to the rigidity of the seal of the round window. The cochlear implant then generates corresponding excitation signals representative of external sounds which are used to stimulate the cochlear nerve.

The microphone is disposed either at an interface with the cochlear fluid, or it is immersed in the cochlear fluid itself. Alternatively, the microphone may be disposed remotely of the cochlear fluid and a conduction means is provided from the fluid to the microphone.

DETAILED DESCRIPTION OF THE INVENTION

In this application the term microphone shall be used generically to designate a device for transducing variations in the pressure of a fluid into corresponding electrical signals.

Figure 1:
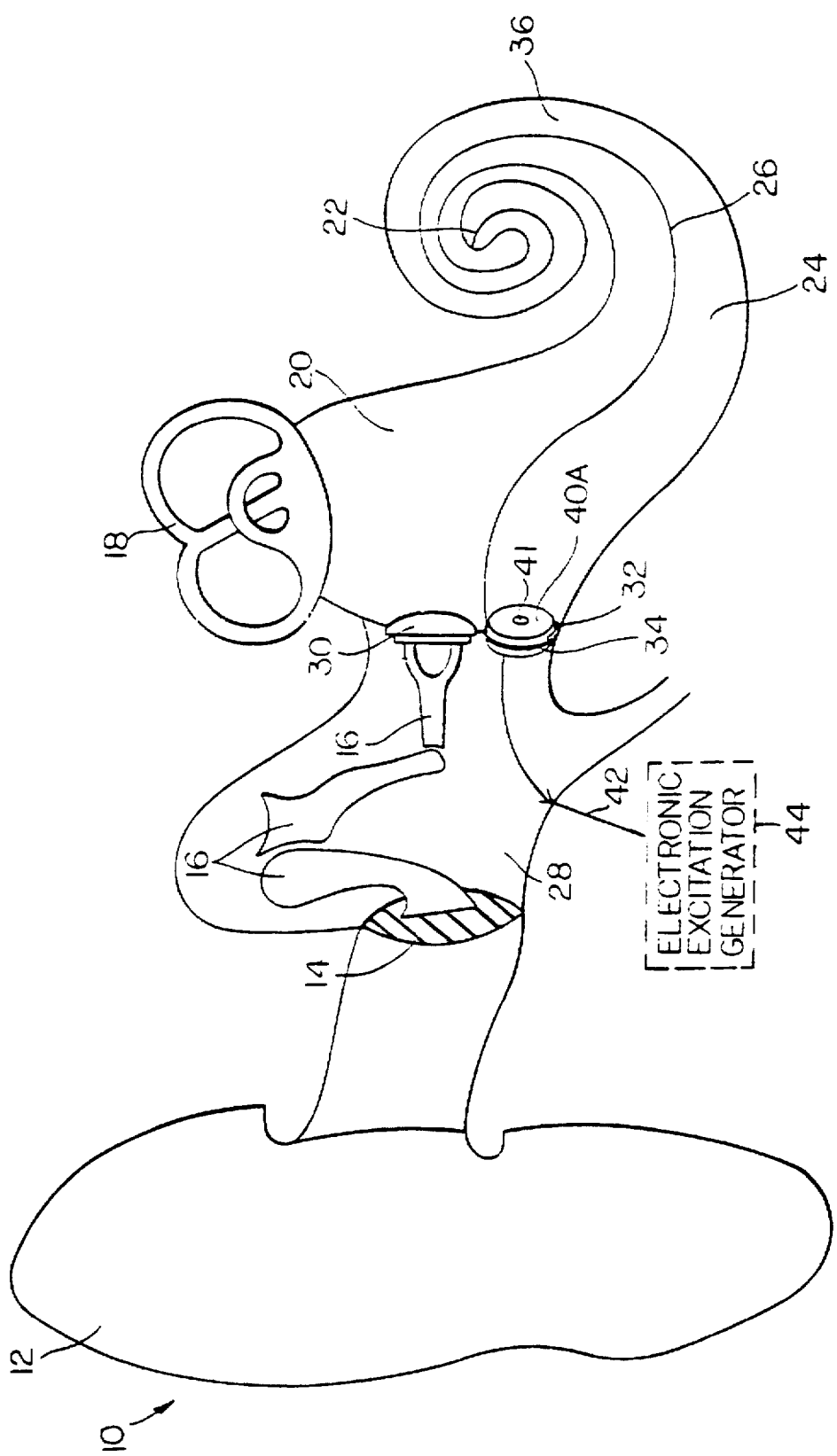
FIG. 1 shows a cross-sectional view of an implanted microphone in accordance with the present invention.

FIG. 1 shows a cross-sectional somewhat diagrammatic view of a patient's ear 10. The ear 10 includes the pinna 12, a tympanic membrane 14, ossicles 16, labyrinth 18, scala vestibuli 20, helicotrema 22, scala tympani 24, and basilar membrane 26. The scala vestibuli 20 and the scala tympani 24 are filled with a cochlear fluid 36. The middle ear 28 communicates with the scala vestibuli through the oval window 30 and with the scala tympani 24 through the round window 32. The fluid is prevented from escaping through the round window 32 by a seal 34, which forms naturally after surgical implantation of the microphone and is formed largely of scar tissue.

In a normal patient, sounds are picked up by the pinna 12 and directed to the tympanic membrane 14 which cause the latter to vibrate. The vibrations of the tympanic membrane 14 are transmitted by the ossicles 16 through the oval window 30 to the scala vestibuli 20. The vibrations are then transmitted to the fluid in the scala tympani 24 through the basilar membrane 26 and the helicotrema 22, to cause corresponding pressure waves. In a normal person, the movements of the basilar membrane 26 corresponding to the pressure waves are translated by the hair cells of the organ of Conti (not shown) into nerve impulses. These nerve impulses travel through the cochlear nerve (not shown) and are interpreted by the brain as sound. As discussed above, in many patients with a sensory neural hearing deficiency or impairment, this path is still intact and only the hair cells are non-functional. Therefore, in accordance with the present invention, the cochlear implant recreates the operation of the hair cells. More specifically, in the embodiment of FIG. 1 a microphone 40A is disposed in the round window 32. The seal insures that the fluid 36 does not flow into the middle ear 28. The microphone 40A is positioned and arranged so that its sensing end 41 is in contact with the fluid 36.

The microphone 40A is connected by a wire 42 to an electronic excitation generator 44. This generator then generates signals to be perceived by the patient corresponding to the pressure variations in fluid 36 sensed by microphone 40A. The generator 44 may be implanted at any medically suitable place within the head of the patient.

Microphone 40A is preferably an electret or ceramic microphone encapsuled in a waterproof casing. Suitable electrode (series EK or EM) and ceramic microphones (series BL) are available from Knowles Electronics, Inc., 1151 Maplewood, Itasca, Ill. 60143, U.S.A.

Figure 2:
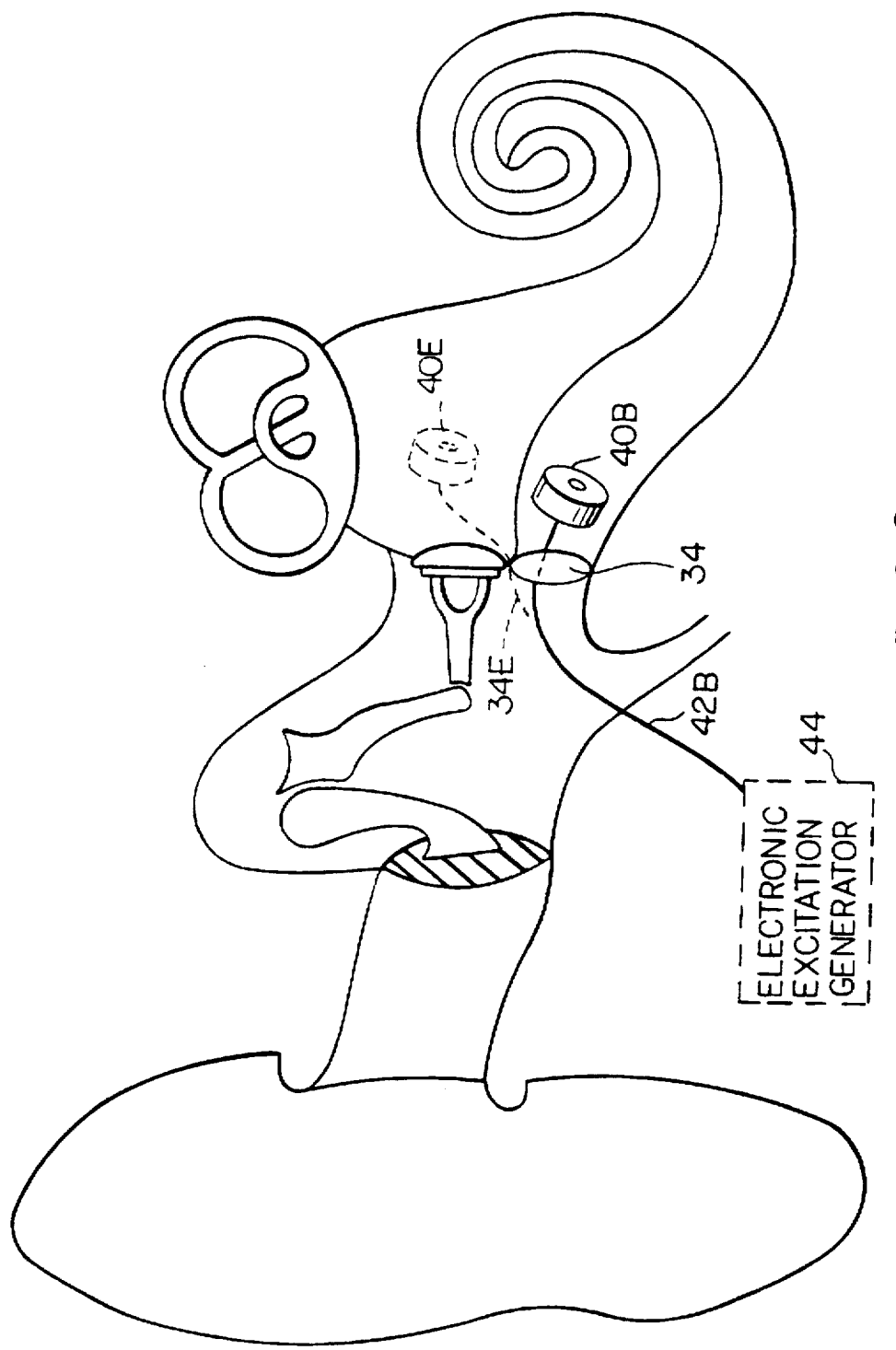
FIG. 2 shows a cross sectional view of a first alternate embodiment of the subject invention.

In an alternate embodiment of the invention shown in FIG. 2, the microphone 40B is immersed in the cochlear fluid 36. Wire 42B extends from the microphone 40B through seal 34 to the electronic excitation generator 44.

Figure 3:
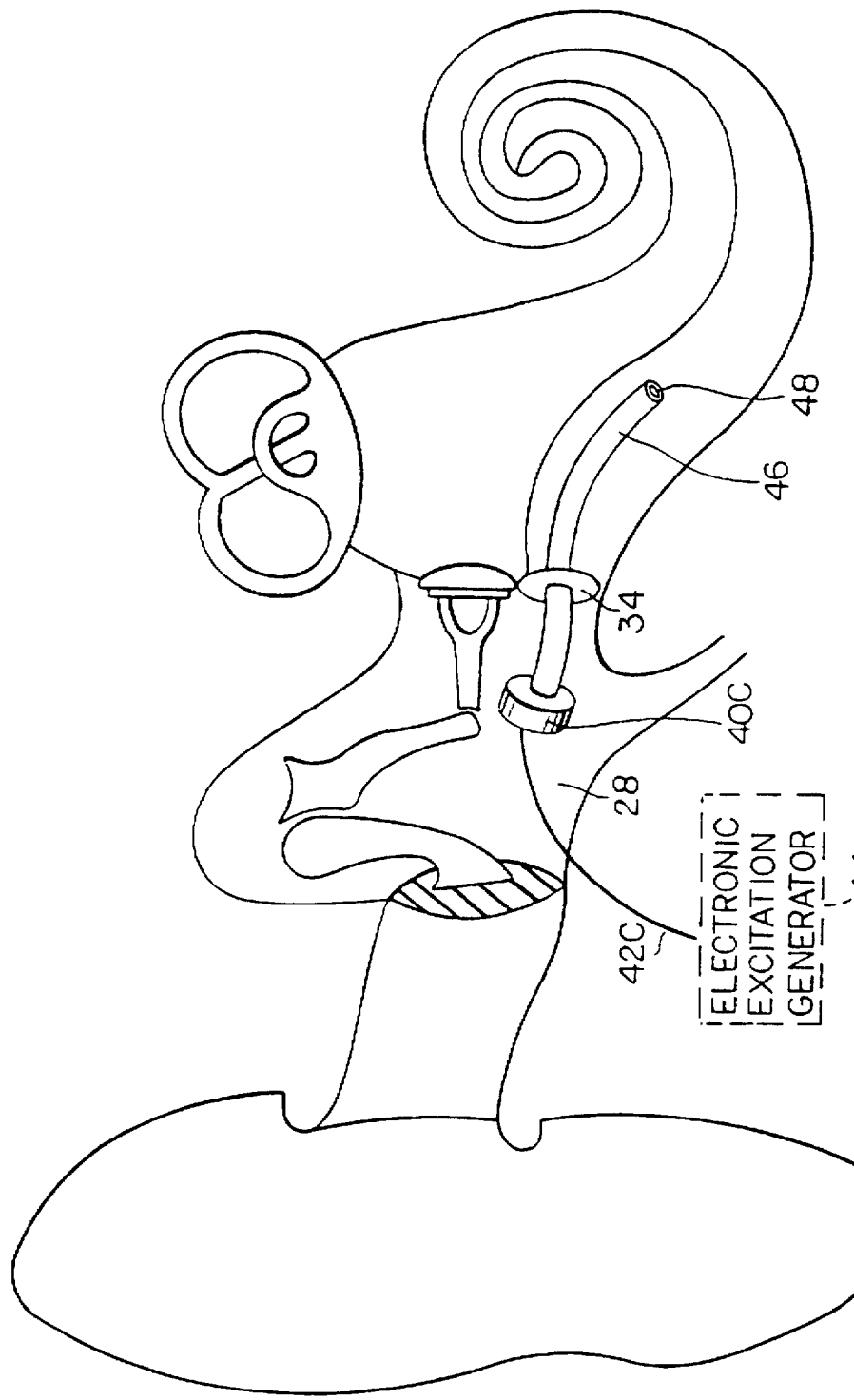
FIG 3. shows a cross sectional view of a second alternate embodiment.

In another embodiment shown in FIG. 3, microphone 40C is disposed in the middle ear 28 of the patient and is connected to the generator 44 by a wire 42C. The microphone 40C is coupled to the fluid 36 by a conduction tube 46 having an open end 48. Tube 46 extends through the seal 34. Preferably tube 46 is free of any air or other gases which may attenuate vibrations sensed in the fluid 36. For this purpose, initially on implantation, the tube 46 is filled with a sterile liquid such as poly-vinyl-alcohol (PVA) silicone rubber, or poly-lactic-acid (PLA). After insertion of the tube 46 into the fluid 36, the PVA is dissolved by the fluid 36. Alternatively, gel-like materials such as silicone rubber which are bio-compatible and do not become liquid in-vitro, can be used, so long as care is taken to select a substance with a close mechanical impedance match to that of the cochlear fluid.

Figure 4:
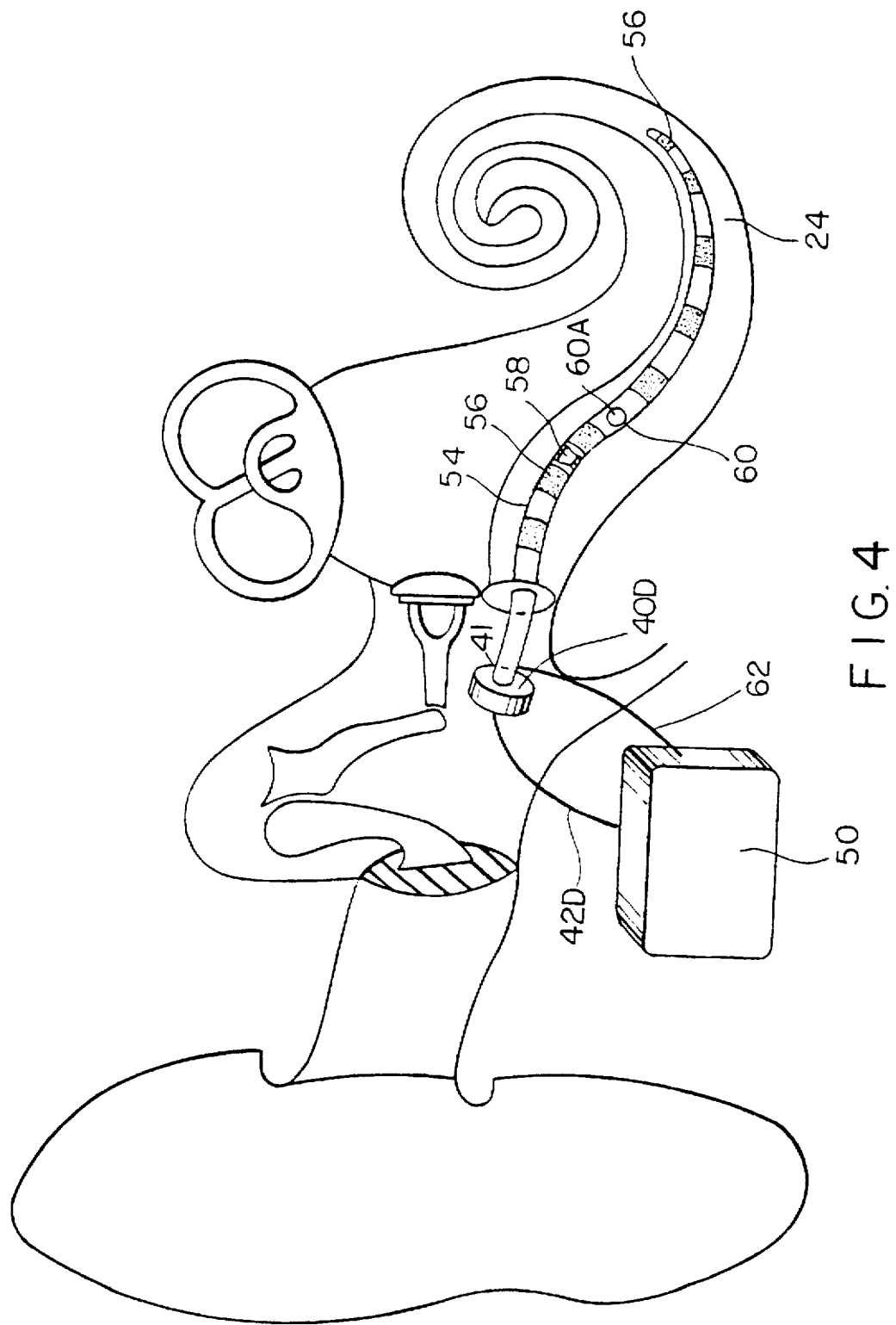
FIG. 4 shows a cochlear implant system using the microphone of FIG. 3.

The excitation generator 44 can be any generator suitable for providing electrical signals to the patient indicative of sounds based on vibrations from the cochlear fluid 36. A specific embodiment wherein the generator is a cochlear implant is shown in FIG. 4. In this Figure, an implanted signal processor and electrode simulator 50 is provided in a common housing, which is connected to a microphone 40D by a wire 42D. Microphone 40D is disposed in the middle ear, like in the embodiment of FIG. 3. Of course the implant 50 works as well with microphones disposed in the round window 32, as shown in FIG. 2, or immersed in the cochlear fluid 34, as shown in FIG. 2.

As is common with such cochlear implants, implant 50 is also provided with an electrode array 54 extending into the scala tympani 24 as shown. The array 54 is provided with a plurality of spaced electrodes 56. Advantageously, electrode array 54 has a hollow tubular shape to define a lumen 58. The lumen 58 terminates adjacent to the sensing surface 41 of microphone 40D to allow the microphone 40D to sense the fluid pressure within the lumen 58. Preferably the lumen 58 is formed with a gap 60 to allow the cochlear fluid 36 to fill the lumen. At implantation, the lumen may be filled with a material such as PVA as discussed above in relation to FIG. 3. A cable 62 extends from the implant 50 and its conductors are imbedded into the electrode array 54 to provide conduction between the implant 50 to the electrodes 56.

In alternate embodiment of the invention, the hole 60 may be replaced by different shaped aperture, or by a plurality of much smaller holes, which may prevent the formation of scar tissues. Scar tissues are undesirable on the hole 60 because they may attenuate the pressure variations.

In yet another embodiment, the lumen may be separated from the cochlear fluid by a permeable membrane 60A which also may prevent scar tissue from growing up through the gap into the lumen. The membrane must be fabricated from a non-osmotic material in order to prevent the build up of an osmotic potential across the membrane, and any associated adverse physiological affects.

In the embodiment of FIG. 4, external sounds produce pressure vibrations in the fluid 36. These pressure variations are sensed by microphone 40D through lumen 58 and hole 60 and result in corresponding electrical signals from the microphone 40D to the implant 50. The implant 50 processes these signals and generates nerve stimulating or excitation signals which are transmitted to the electrodes 56 by cable 62. The electrodes 56 apply these signals to the cochlear nerve (not shown).

If the round window is unsuitable, a microphone 40E may be placed in a surgically created hole 34E in the cochlea, or in the scala vestibuli as shown in phanton lines in FIG. 2.

Although the invention has been described with reference to several particular embodiments, it is to be understood that these embodiments are merely illustrative of the application of the principles of the invention. Accordingly, the embodiments described in particular should be considered exemplary, not limiting, with respect to the following claims.

I claim:

1. A system for aiding a person having hearing deficiency, said system comprising:

a microphone for implantation into said person;

a coupler for coupling pressure variations in a cochlear fluid of said person, said microphone being constructed and arranged to sense said pressure variations, and to generate corresponding electrical signals; and a generator for generating excitation signals for said person corresponding to said electrical signals.

2. The system of claim 1 wherein said microphone is disposed in an opening of the cochlea of said person.

3. The system of claim 1 wherein said microphone is immersed into said cochlear fluid.

4. The system of claim 1 wherein said person has a body cavity containing said cochlear fluid, and wherein said microphone is disposed outside said cavity.

5. The system of claim 4 wherein said coupler includes a tube extending from said microphone to said fluid for transmitting said pressure vibrations to said microphone.

6. A cochlear implant system for implantation into a patient, said system comprising:

an implanted microphones;

a coupler being adapted for coupling pressure variations in a cochlear fluid of said patient to said implanted microphone, said implanted microphone being constructed and arranged to sense said pressure variations and to generate electrical signals indicative of said pressure variations;

an electrode array adapted to provide excitation of a cochlear nerve of said patient; and a signal processor receiving said electrical signals to generate corresponding excitation signals for said electrode.

7. The system of claim 6 wherein said microphone is disposed in the middle ear.

8. The system of claim 7 wherein said coupler includes a conduction tube extending from a body cavity containing cochlear fluid to said microphone for transmitting said pressure vibrations.

9. The system of claim 8 wherein said cavity is the scala tympani.

10. The system of claim 8 wherein said cavity is the scala vestibuli.

11. The system of claim 6 wherein said electrode is a tubular electrode.

12. The system of claim 11 wherein said tubular electrode extends from said microphone to a cavity containing cochlear fluid.

13. The system of claim 12 wherein said tubular electrode is formed with a gap to allow cochlear fluid to enter into said tubular electrode.

14. The system of claim 12 wherein said tubular electrode is formed with several holes to allow cochlear fluid to enter into said tubular electrode.

15. The system of claim 12 wherein said tubular electrode is formed with a permeable membrane to allow pressure changes to be transmitted.

16. A method for producing excitation signals for a patient having a hearing deficiency, said electrical signals being indicative of ambient sounds, comprising the steps of:

implanting a microphone inside a patient, said microphone being coupled to a cochlear fluid of said patient, said microphone sensing pressure variations in said cochlear fluid due to said ambient sounds;

generating electrical signals with said microphone indicative of said pressure variations; and processing said electrical signals to generate said excitation signals.

17. The method of claim 16 wherein said microphone is disposed in a round window.

18. The method of claim 16 wherein said microphone is implanted in the scala tympani of the patient to immerse said microphone in cochlear fluid.

19. The method of claim 16 wherein said microphone is implanted into the scala vestibuli.

20. The method of claim 16 wherein said microphone is inserted into the middle ear of the patient, with a tube extending from said microphone to said cochlear fluid to transmit said variations.

21. The method of claim 16 further comprising the step of implanting a cochlear signal processor in said patient, said cochlear signal processor receiving said electrical signals and generating said excitation signals in response.

* * * * *